United States Patent
Mori et al.

(10) Patent No.: US 12,420,108 B2
(45) Date of Patent: Sep. 23, 2025

(54) MAGNETIC STIMULATION DEVICE

(71) Applicant: IFG CORPORATION, Miyagi (JP)

(72) Inventors: Hitoshi Mori, Miyagi (JP); Kenji Yashima, Miyagi (JP); Hitoshi Kagaya, Aichi (JP); Shinichi Izumi, Miyagi (JP)

(73) Assignee: IFG CORPORATION, Miyagi (JP)

( * ) Notice: Subject to any disclaimer, the term of this patent is extended or adjusted under 35 U.S.C. 154(b) by 969 days.

(21) Appl. No.: 17/614,959

(22) PCT Filed: Jan. 8, 2020

(86) PCT No.: PCT/JP2020/000257
§ 371 (c)(1),
(2) Date: Nov. 29, 2021

(87) PCT Pub. No.: WO2021/140585
PCT Pub. Date: Jul. 15, 2021

(65) Prior Publication Data
US 2022/0249858 A1 Aug. 11, 2022

(51) Int. Cl.
*A61N 2/02* (2006.01)
*A61N 2/00* (2006.01)
(Continued)

(52) U.S. Cl.
CPC ............ *A61N 2/02* (2013.01); *A61N 2/006* (2013.01); *H01F 27/025* (2013.01); *H01F 27/085* (2013.01); *H01F 27/245* (2013.01)

(58) Field of Classification Search
CPC ........ A61N 2/02; A61N 2/006; H01F 27/025; H01F 27/085; H01F 27/245; H01F 7/20; H01F 27/2876
See application file for complete search history.

(56) References Cited

U.S. PATENT DOCUMENTS

| | | | |
|---|---|---|---|
| 4,056,097 A | 11/1977 | Maass | |
| 2011/0021863 A1* | 1/2011 | Burnett | A61N 2/006 600/13 |

FOREIGN PATENT DOCUMENTS

| | | |
|---|---|---|
| EP | 0906136 A1 | 4/1999 |
| EP | 3332837 A1 | 6/2018 |

(Continued)

OTHER PUBLICATIONS

Supplementary European Search Report dated Dec. 8, 2022 for the corresponding patent application No. 20912338.9.
(Continued)

*Primary Examiner* — Carrie R Dorna
*Assistant Examiner* — Joshua Daryl D Lannu
(74) *Attorney, Agent, or Firm* — LUCAS & MERCANTI, LLP

(57) ABSTRACT

A magnetic stimulator includes a magnetic core, conductors, and a casing. The magnetic core includes a body portion, and leg parts that protrude in the same direction from the body portion. The conductors are wound in a coil manner respectively around the leg parts. The casing is a container for housing the magnetic core and the conductors. The leg parts of the magnetic core are formed such that cross-sectional areas thereof that are parallel to a plane which simultaneously crosses the leg parts gradually decrease from base parts on the body portion side toward tips.

6 Claims, 15 Drawing Sheets

(51) Int. Cl.
*H01F 7/20* (2006.01)
*H01F 27/02* (2006.01)
*H01F 27/08* (2006.01)
*H01F 27/245* (2006.01)
*H01F 27/28* (2006.01)

(56) References Cited

FOREIGN PATENT DOCUMENTS

| | | | |
|---|---|---|---|
| JP | 2010-166971 A | 8/2010 | |
| JP | 5289640 B1 | 9/2013 | |
| JP | 2016-028640 A | 3/2016 | |
| JP | 6535825 B1 | 6/2019 | |
| TW | 201429512 A * | 8/2014 | |
| WO | WO-2016013146 A1 * | 1/2016 | ............... A61N 2/00 |

OTHER PUBLICATIONS

PCT, International Search Report for the corresponding patent application No. PCT/JP2020/000257, dated Mar. 10, 2020, with English translation.
National Intellectual Property Administration of P.R. China, "Notification of first review comments" mailed Feb. 4, 2024, which was issued for the corresponding Chinese patent application No. 202080032235.2 with English translation (14 pages).

* cited by examiner

[FIG. 1]
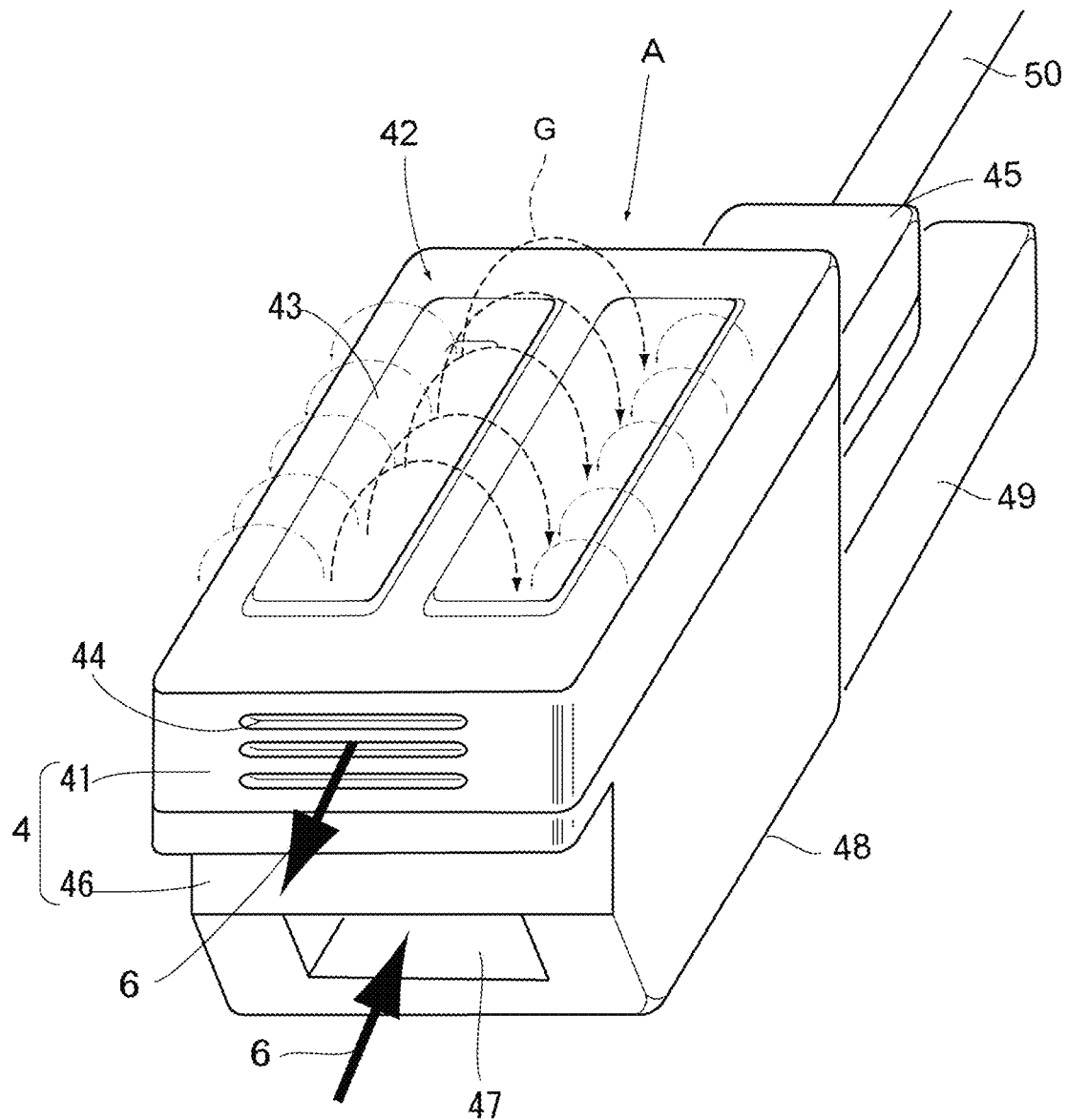

[FIG. 2]
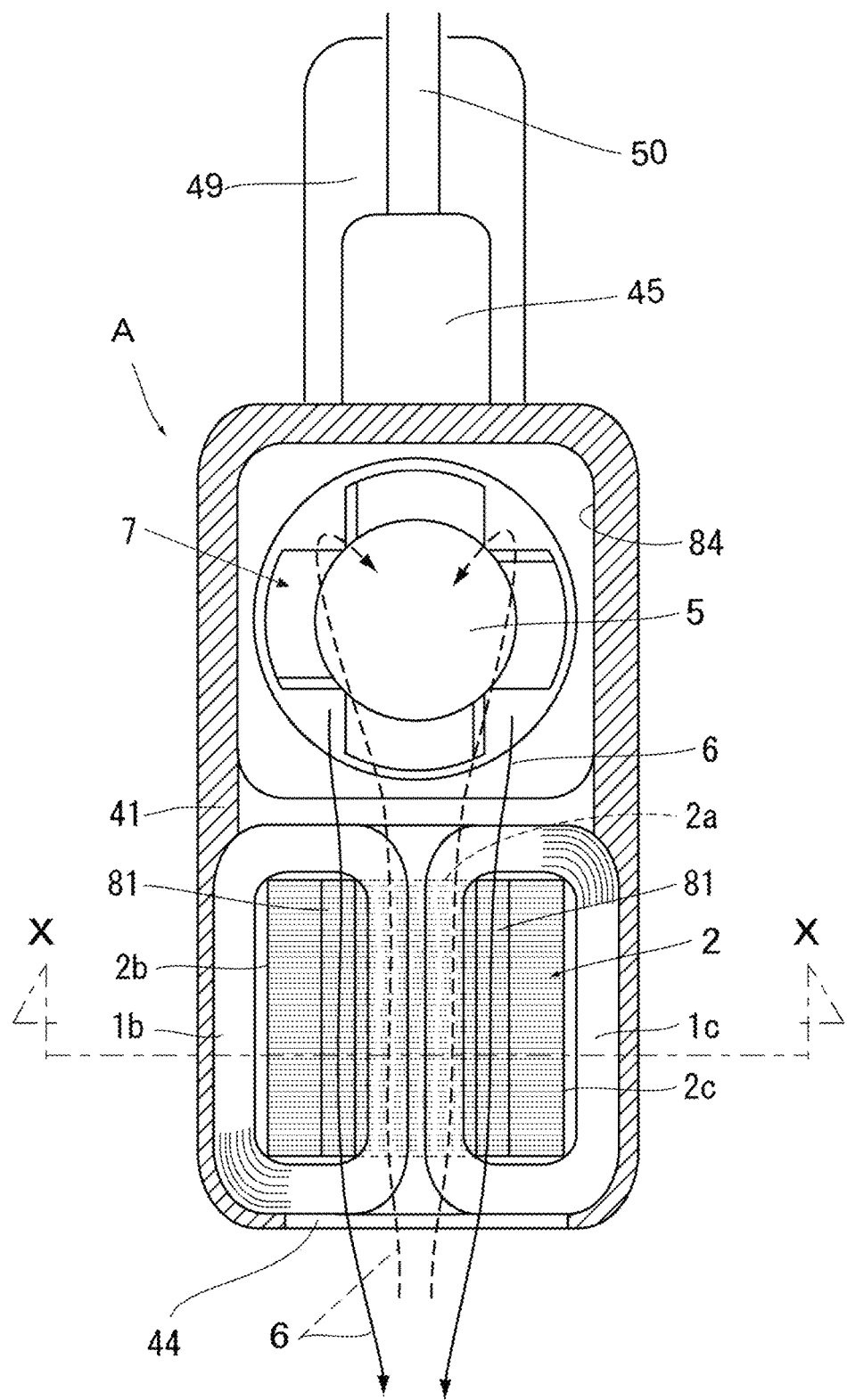

[FIG. 3]
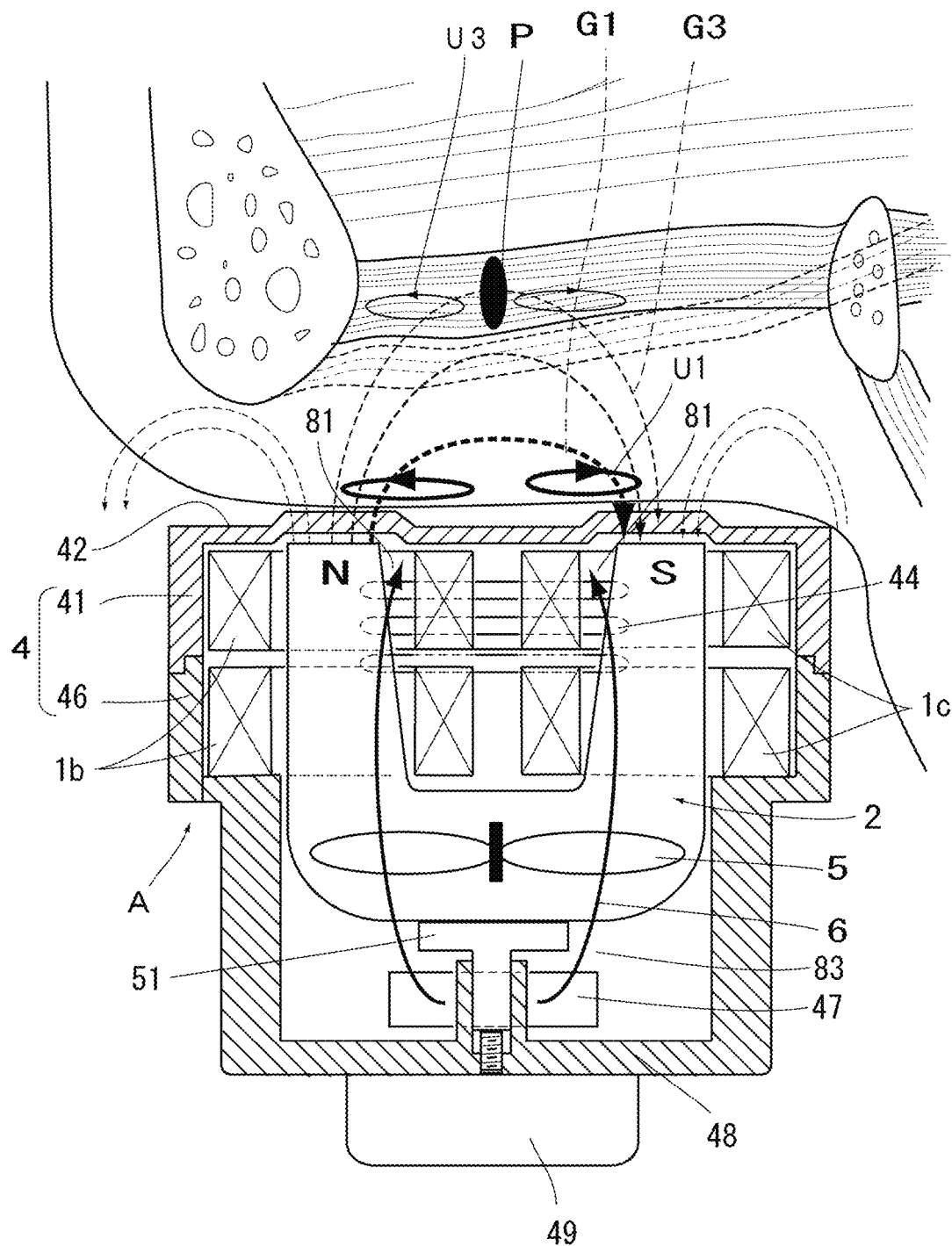

[FIG. 4]
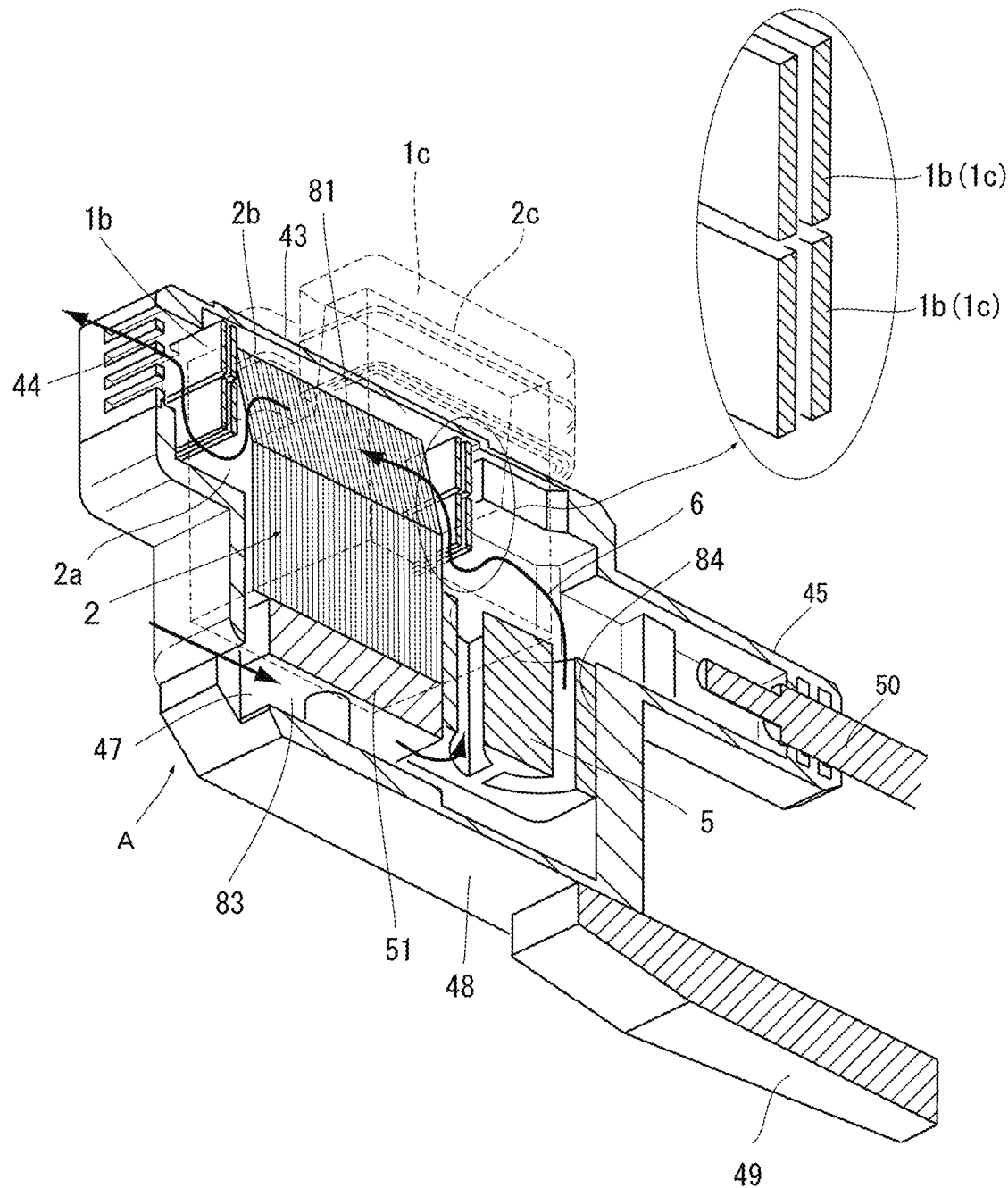

[FIG. 5]
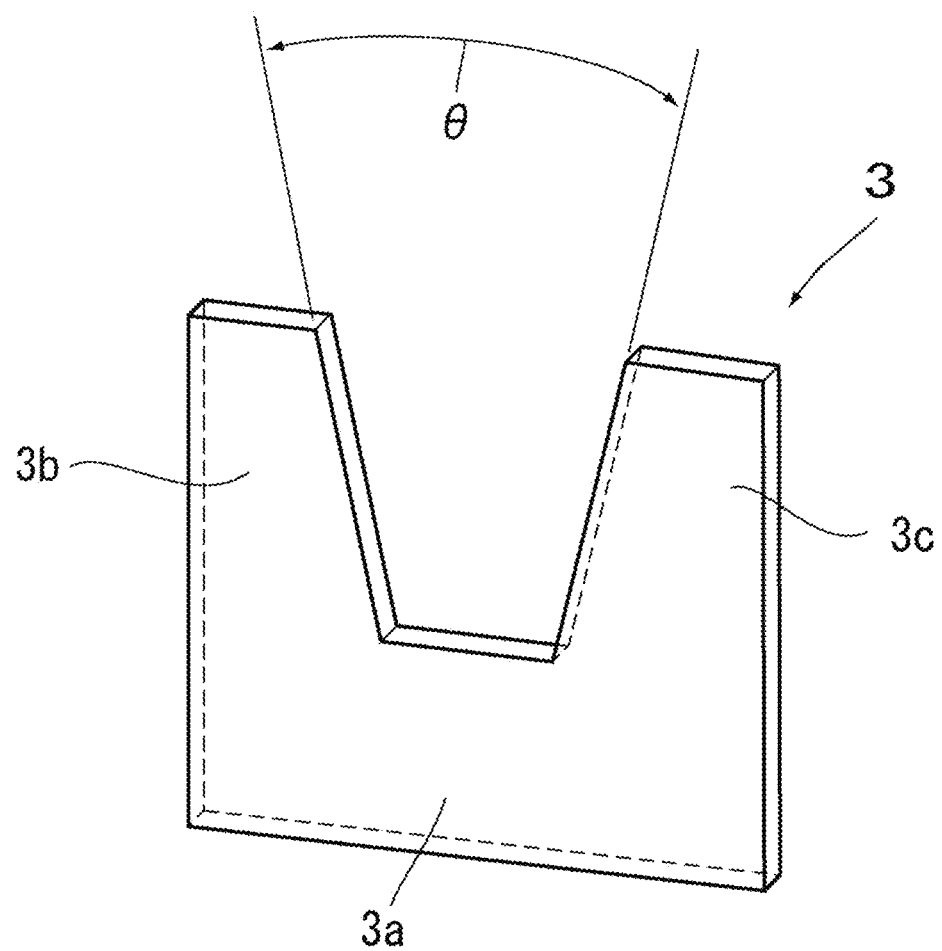

[FIG. 6]
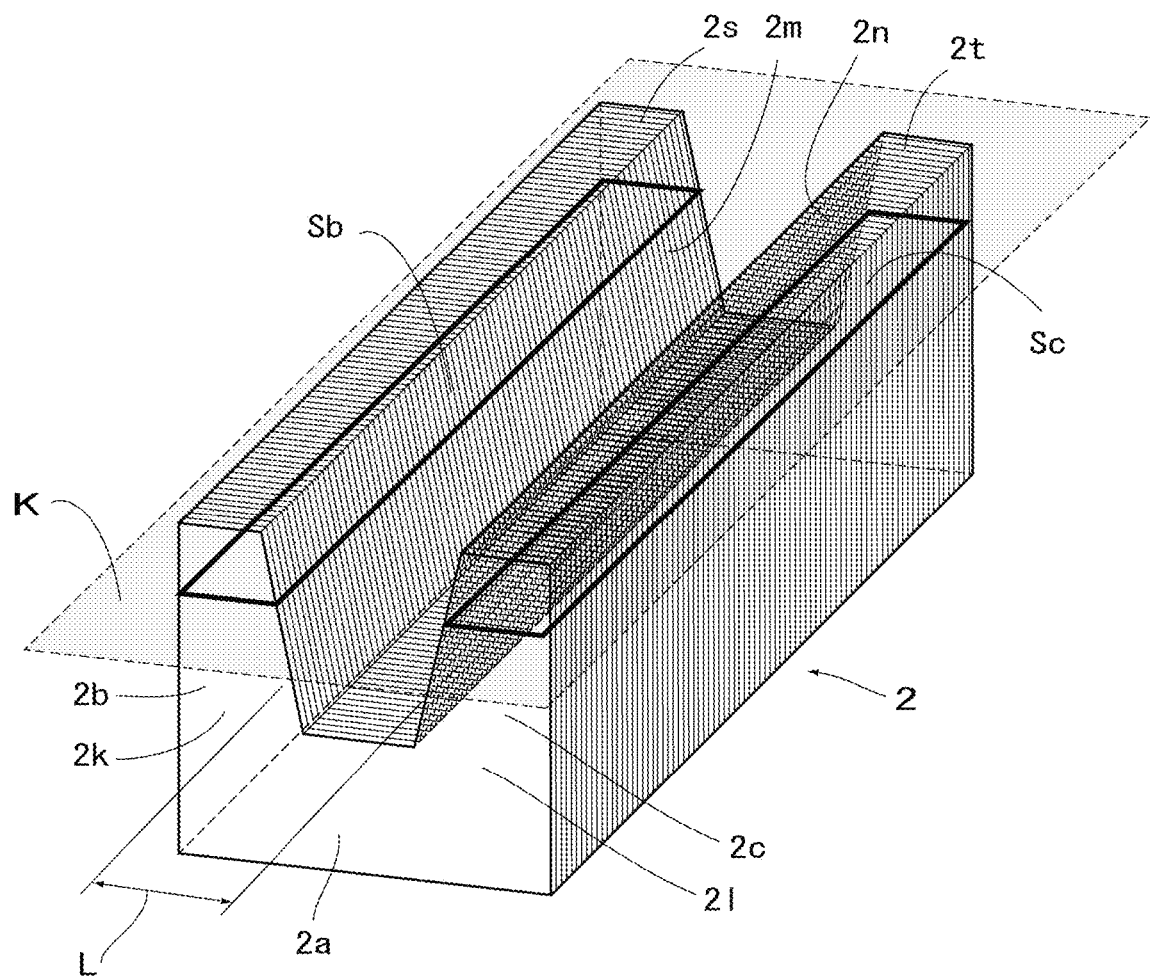

[FIG. 7]
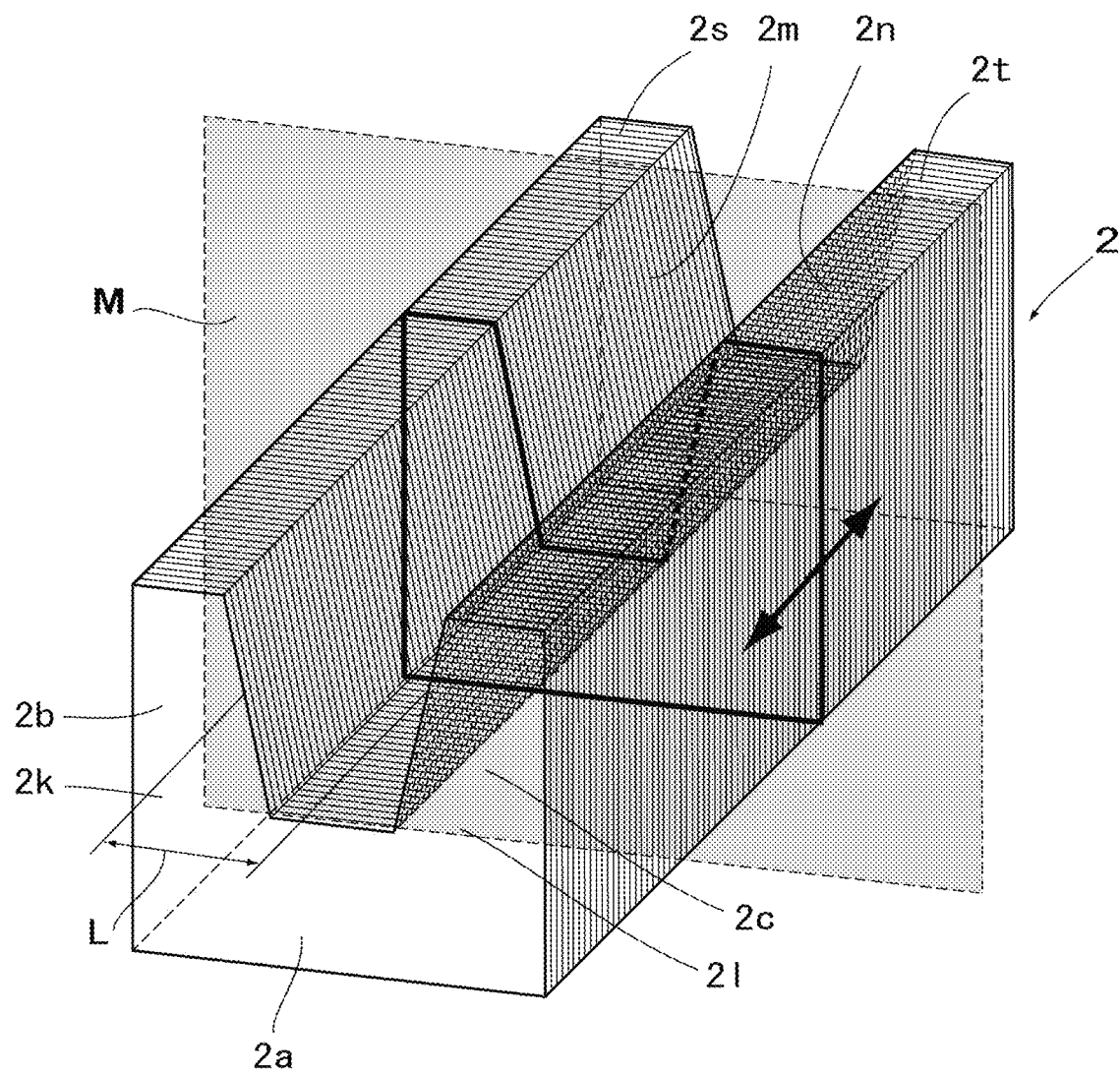

[FIG. 8]
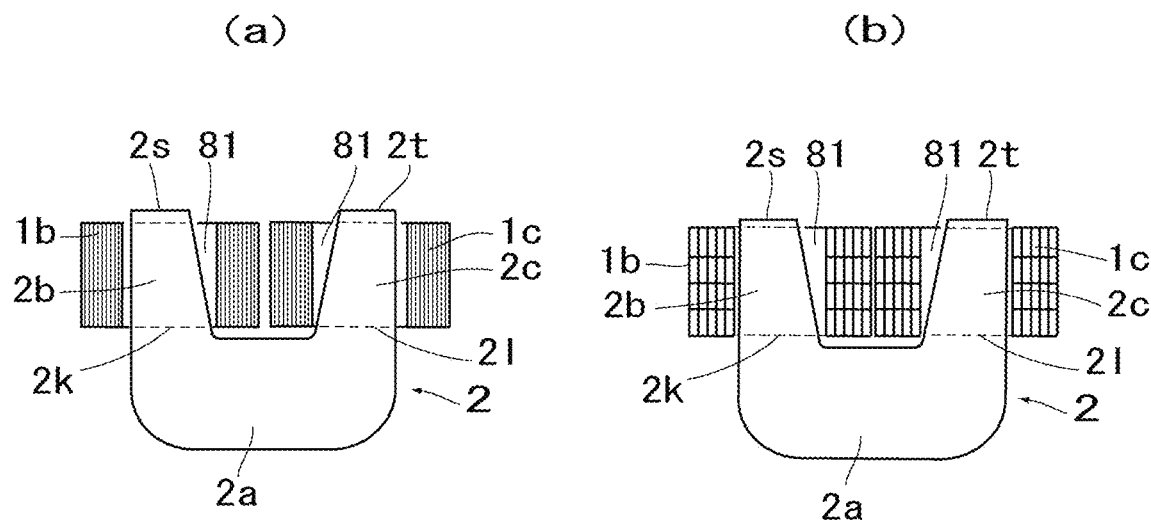

[FIG. 9]
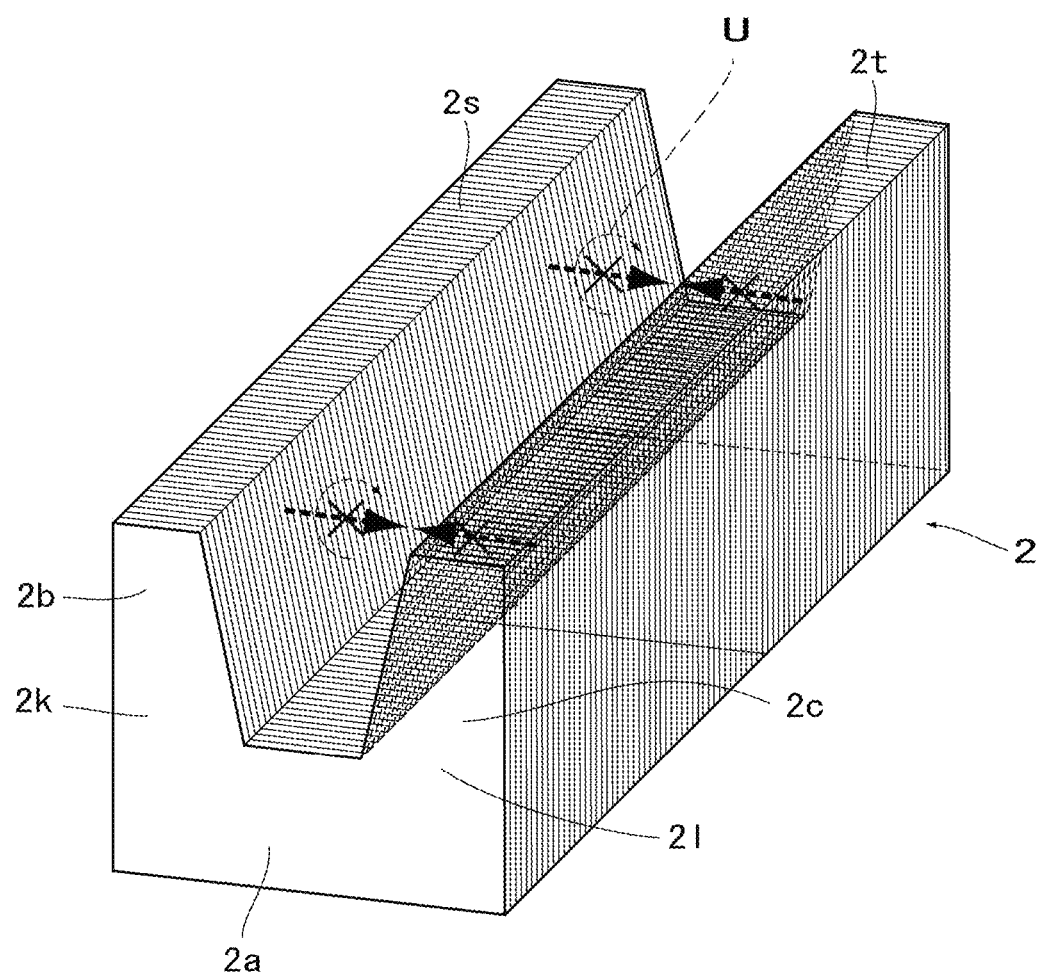

[FIG. 10]
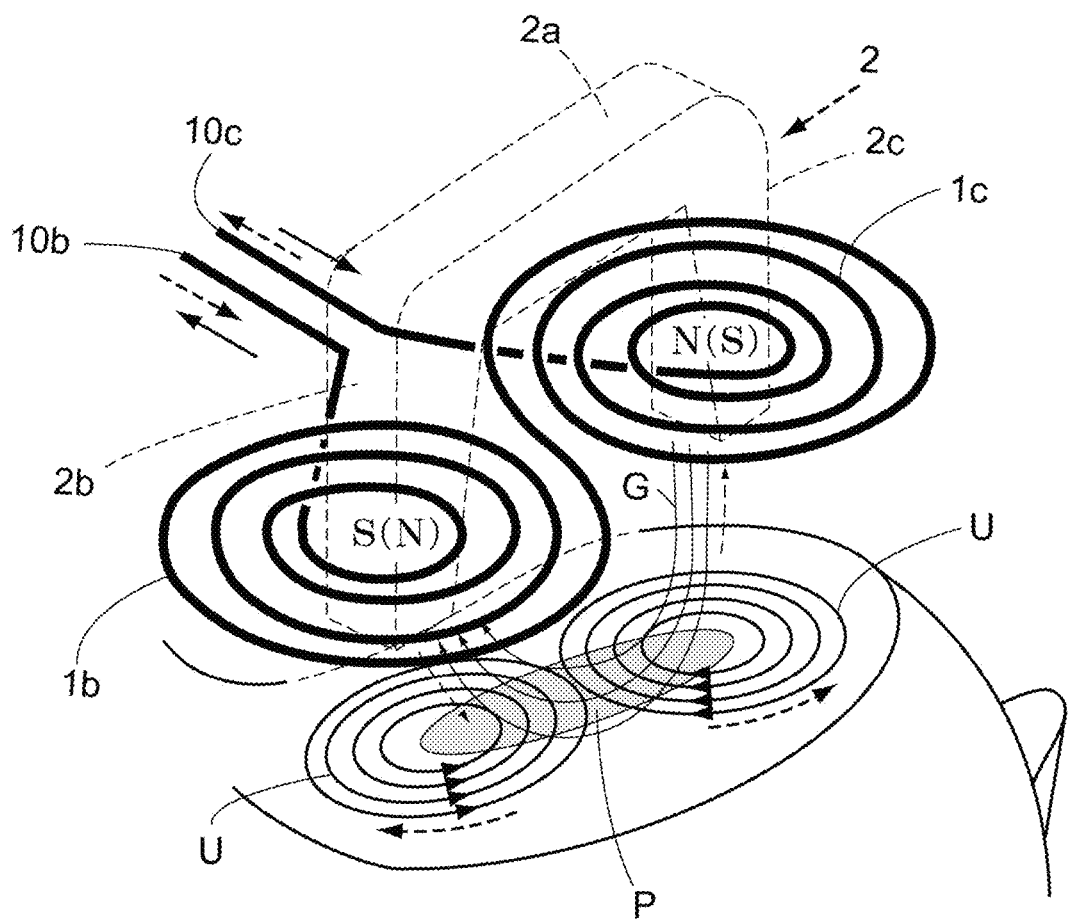

[FIG. 11]
(a)
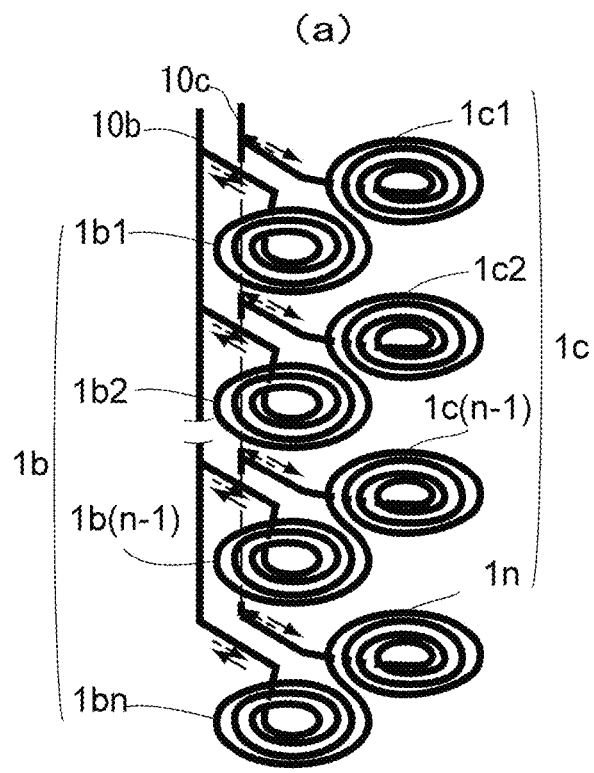
(b)
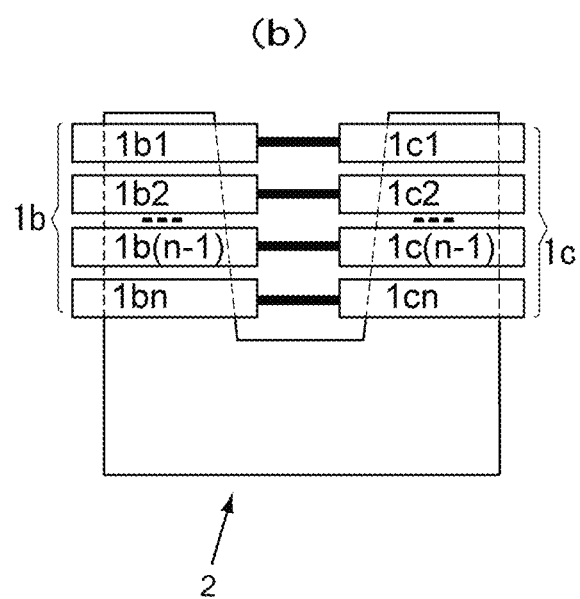

[FIG. 12]
(a)
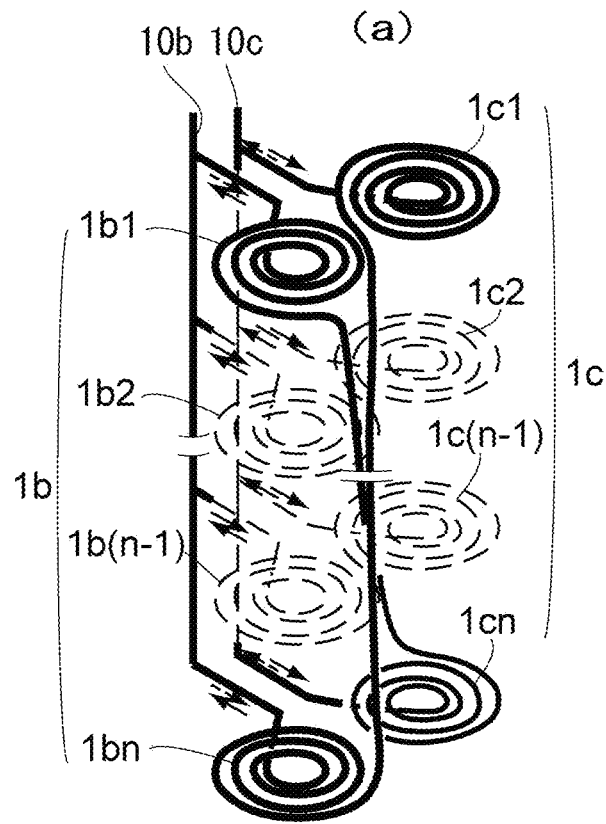
(b)
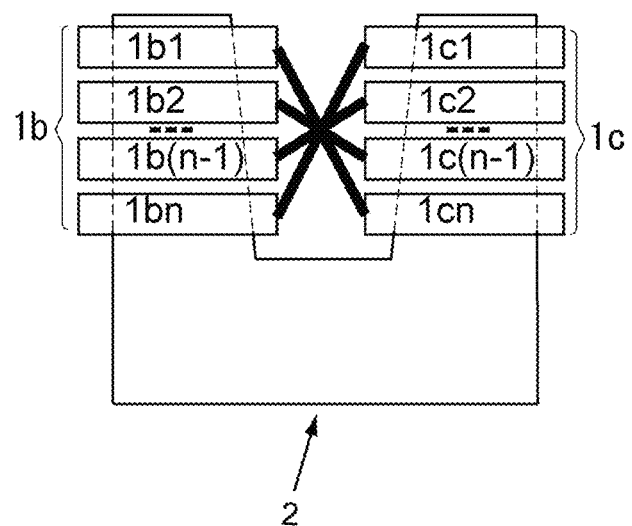

[FIG. 13]
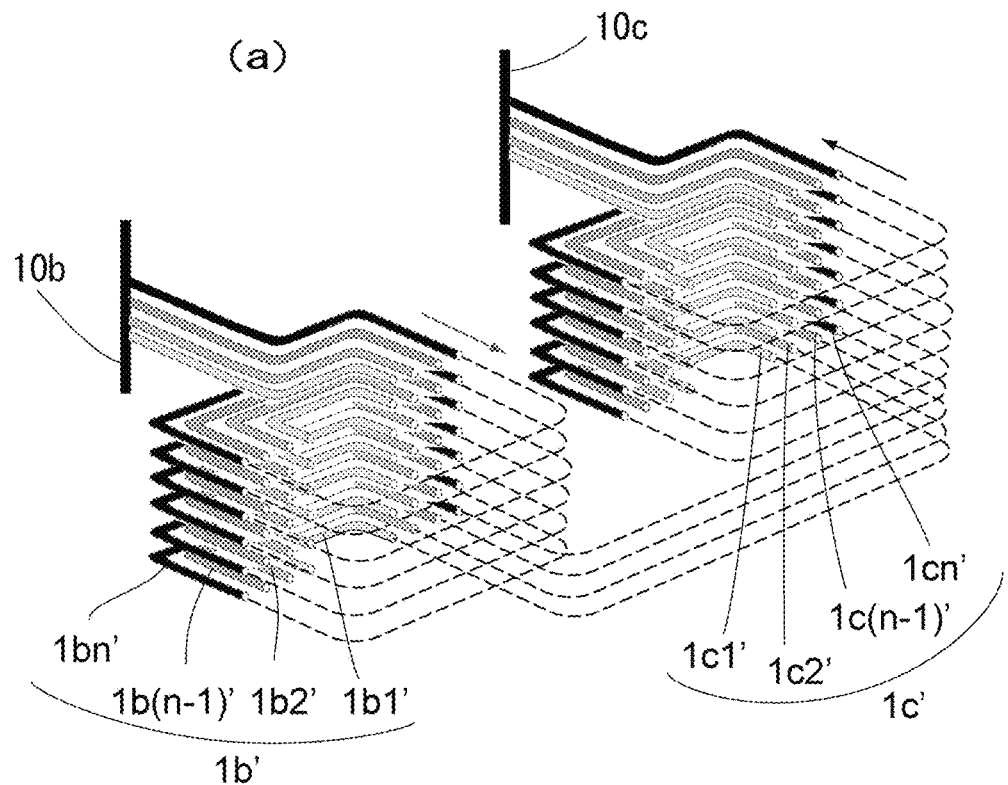
(a)
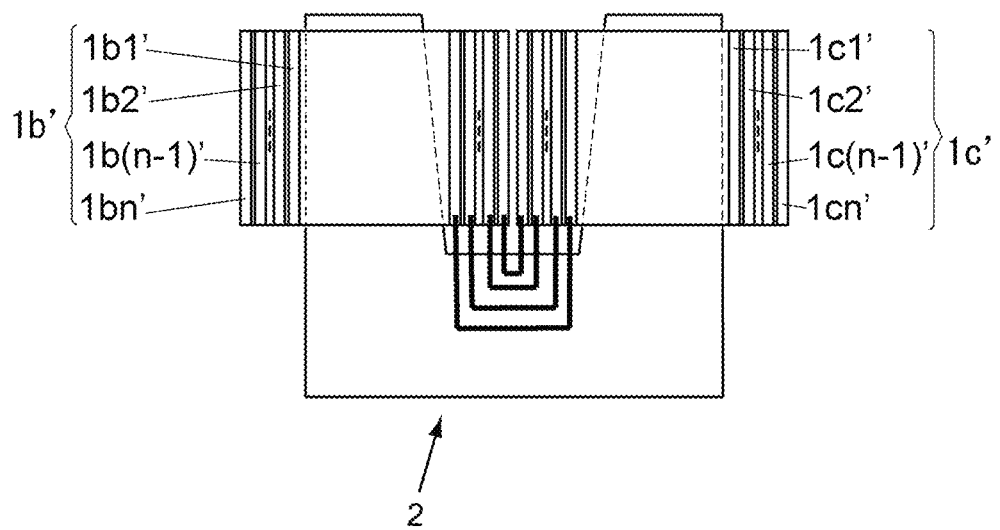
(b)

[FIG. 14]
(a)
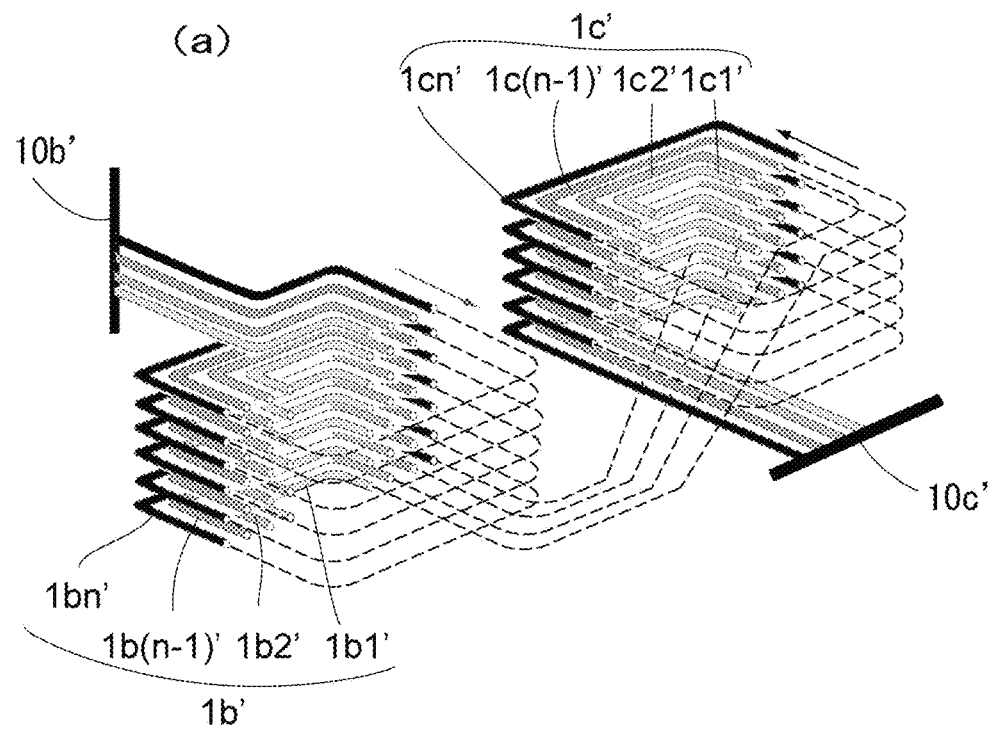
(b)
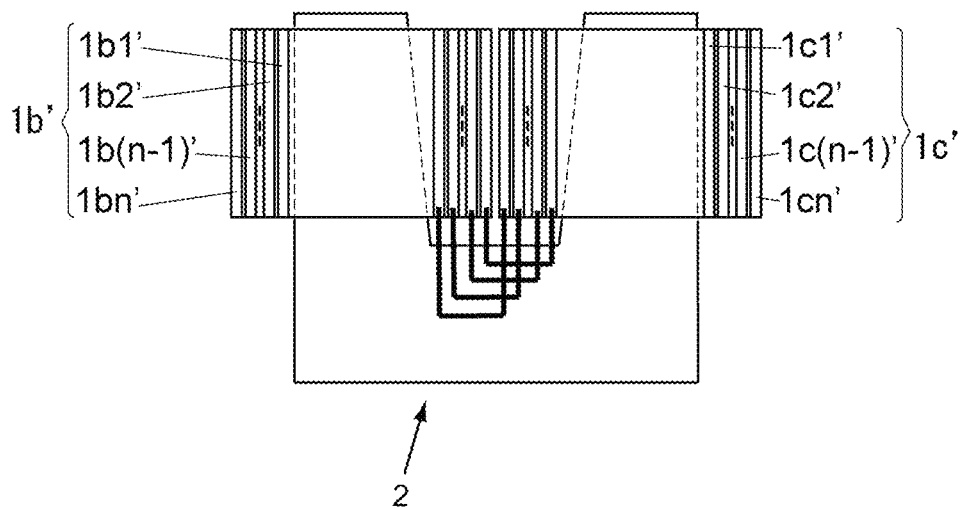

[FIG. 15]
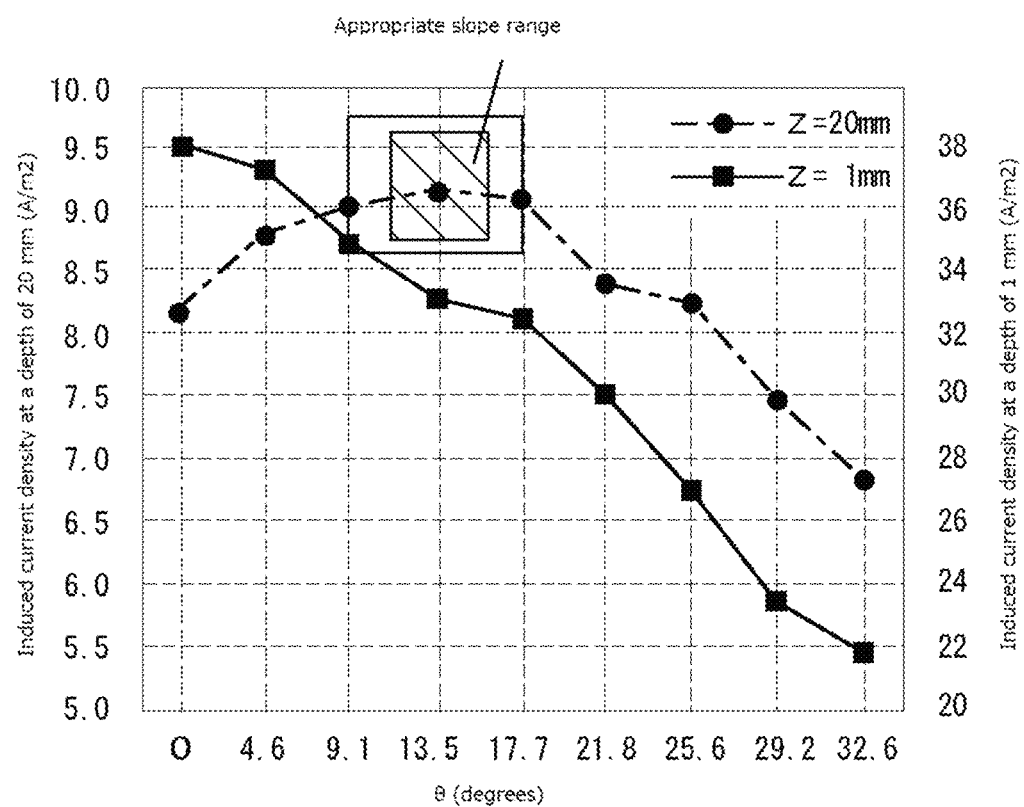

MAGNETIC STIMULATION DEVICE

CROSS REFERENCE TO RELATED APPLICATION

This Application is a 371 of PCT/JP2020/000257 filed on Jan. 8, 2020, and the above application is incorporated herein by reference.

TECHNICAL FIELD

The present invention relates to a magnetic stimulation device used for repeatedly applying magnetic stimulation to peripheral nerves in an affected region or motor areas of cerebral cortex to enhance motor function.

BACKGROUND ART

More than two million people are now suffering from paralysis of their limbs caused by cerebral strokes and spinal cord injuries, and the number of such paralytic patients is still increasing due to a change in the age structure of the Japanese population. Since paralysis persisting for a long period of time due to brain damage can cause a significant decrease in muscle function as a result of disuse syndrome, it is difficult for the patient to recover from the paralysis.

Rehabilitation as a type of exercise therapy is considered to be the most important treatment to prevent disuse syndrome caused by hemiplegia or quadriplegia and to actively promote recovery of muscle function.

Dysphagia (difficulty in swallowing) as sequelae of cerebrovascular disorders or caused by aging is also becoming a social problem. The majority of pneumonia cases (pneumonia accounts for 7.2% of causes of death in Japan) are aspiration pneumonia cases caused by dysphagia. As a means of rehabilitation for dysphagia, exercise therapy such as repetitive activation of swallowing-related muscles is often used.

One of the methods for stimulating peripheral nerves or motor areas of cerebral cortex to induce movement of muscles is magnetic stimulation. In this technique, when a pulse current is supplied to a coil placed near the surface of a body to cause the coil to generate a magnetic flux, a current is induced in the body by the magnetic flux and the induced current stimulates the nerves to activate the muscles.

Patent Literature 1 discloses a technique for bending a finger or an arm repeatedly by magnetic stimulation. Patent Literature 1 indicates that when magnetic pulses are applied at intervals of 10 milliseconds to magnetically stimulate the nerves of the arm, the arm's bending distance increases as the number of pulses increases. However, since a large current must be supplied to the magnetic stimulation device, the temperature of the device is likely to increase.

Patent Literature 2 discloses a technique for air-cooling a magnetic stimulation device so as to suppress a temperature rise of a coil and a magnetic core caused by heat generation during current supply and thereby allow continuous magnetic stimulation to be applied many times.

CITATION LIST

Patent Literature

[Patent Literature 1] Japanese Unexamined Patent Application Publication No. 2010-166971

[Patent Literature 2] Japanese Unexamined Patent Application Publication No. 2016-28640

SUMMARY OF INVENTION

Technical Problem

The effect of magnetic stimulation increases as the number of repetitions of magnetic stimulation increases. However, a large current of more than several hundred amperes must be passed through a coil to cause effective magnetic stimulation to occur. Therefore, magnetic stimulation using successive pulses has a drawback that significant heat generation and temperature rise occur in the coil, as described above, and thus only air-cooling cannot be a solution and the number of pulses cannot be increased to a desired value. This heat generation of the coil is a serious technical limitation of the continuous magnetic stimulation.

There is another limitation for this magnetic stimulation device, a limitation in an environment where the device is used. In the field of rehabilitation, the time that can be actually allocated to the rehabilitation treatments is limited to 20 minutes per treatment. Since preparation time is also needed, the actual rehabilitation time is about 15 minutes. Magnetic stimulation must be repeated a required number of times within this time period. The current specifications require to perform 100 sessions of magnetic stimulation within 15 minutes with 60 magnetic pulses per each session of magnetic stimulation. This means that the number of magnetic pulses required within the actual rehabilitation time is 6000. In addition, the safety standards for medical devices require that the temperature of the surface of a device to be in contact with the skin of a patient for a long time be lower than 43° C. Therefore, small magnetic stimulation devices (for example, a device for stimulating jaws to be described later) also must meet this requirement.

This type of magnetic stimulation device is not always a large one for stimulating muscles of a large part of the body such as an arm and a leg, and is sometimes used for stimulating a jaw. Since the device is used for stimulating the jaws of the patients including elderly and female patients, a certain percentage of whom have small jaws, smaller magnetic devices are needed.

A smaller device consequently has a smaller coil with a lower heat capacity and therefore causes a temperature rise of the coil. Since a reduction in the size of the coil leads to a reduction in the magnitude of the magnetic flux, the device with a smaller coil must generate a higher magnetic flux density to produce stimulation equivalent to that produced by a larger magnetic stimulation device. In other words, since a larger electric current must be supplied to the smaller coil, the temperature of the coil increases further.

For the above reasons, it is difficult for conventional magnetic stimulation devices to keep their surface temperature lower than 43° C., and there is no choice but to reduce their magnetic flux densities. In particular, a reduction in the size of the device results in a significant increase in the surface temperature of the device. Therefore, a reduction in the size of magnetic stimulation devices that meet the above specifications cannot be achieved.

The present invention has been made in view of these conventional technical problems, and it is an object of the present invention to make practical use of a magnetic stimulation device, regardless of whether it is large or small in size, that can suppress a temperature rise caused by heat generation during current supply below a safety standard and thus allows continuous magnetic stimulation to be applied many times.

Solution to Problem

1. One Embodiment Relates to an Improvement in a Magnetic Core 2 of a Magnetic Stimulation Device A (FIG. 6).
   The magnetic stimulation device A includes:
   a magnetic core 2 including: a core body 2*a*; and first and second legs 2*b*, 2*c* extending in one direction from the core body 2*a*;
   conductors 1*b*, 1*c* (1*b*', 1*c*') including: a conductor 1*b* (1*b*') that is wound around the first leg 2*b* in a coil shape; and a conductor 1*c* (1*c*') that is wound around the second leg 2*c* in a coil shape; and
   a casing 4 that houses the magnetic core 2 and the conductors 1*b*, 1*c* (1*b*', 1*c*').
   In the magnetic stimulation device A,
   the first and second legs 2*b*, 2*c* each have such a shape that a distance L between opposite medial surfaces 2*m*, 2*n* of the legs 2*b*, 2*c* gradually increases from a base 2*k*, 2*l* of the leg 2*b*, 2*c* near the core body 2*a* to a tip 2*s*, 2*t* of the leg 2*b*, 2*c*, and thereby the first and second legs 2*b*, 2*c* each have such a shape that a cross-sectional area Sb, Sc of the leg 2*b*, 2*c* parallel to a plane K passing horizontally through both of the legs 2*b*, 2*c* gradually decreases from the base 2*k*, 2*l* to the tip 2*s*, 2*t*.

2. Another Embodiment Relates to a Stacking Direction of Thin Sheets 3 of the Magnetic Core 2 (FIG. 7).
   In the magnetic stimulation device A according to item 1,
   the magnetic core 2 is a stack of thin sheets 3, and a surface of each of the stacked sheets 3 is parallel to a plane M passing vertically through both of the core body 2*a* and the legs 2*b*, 2*c* of the magnetic core 2.

3. Another embodiment relates to the casing 4 of the magnetic stimulation device A.
   The Magnetic Stimulation Device a According to Item 1 or 2 further includes a cooling space 81 designed to allow a cooling gas 6 taken into the casing 4 to flow through, between the medial surface 2*m*, 2*n* of each of the legs 2*b*, 2*c* and a surface of the conductor 1*b*, 1*c* wound around the leg 2*b*, 2*c* to face the medial surface 2*m*, 2*n*.

4. Another Embodiment Relates to the Conductors 1*b*, 1*c* of the Magnetic Stimulation Device a (Straight Connection structure of a first embodiment: FIG. 11).
   In the magnetic stimulation device A according to any one of items 1 to 3,
   each of the conductors 1*b*, 1*c* is divided into a plurality of layers (levels), each of which is formed of a wire, and the wires 1*b*1-1*bn*/1*c*1-1*cn* of the layers are wound around the leg 2*b*, 2*c* in an order from the tip 2*s*, 2*t* to the base 2*k*, 2*l* of the leg 2*b*, 2*c*, and
   the wires 1*b*1-1*bn* each wound around the first leg 2*b* in a given layer (level) are respectively connected to the wires 1*c*1-1*cn* each wound around the second leg 2*c* in a layer adjacent to the given layer.

5. Another Embodiment Relates to the Conductors 1*b*, 1*c* of the Magnetic Stimulation Device a (Cross Connection Structure of the First Embodiment: FIG. 12).
   In the magnetic stimulation device A according to any one of items 1 to 3,
   each of the conductors 1*b*, 1*c* is divided into a plurality of layers (levels), each of which is formed of a wire, and the wires 1*b*1-1*bn*/1*c*1-1*cn* of the layers are wound around the leg 2*b*, 2*c* in an order from the tip 2*s*, 2*t* to the base 2*k*, 2*l* of the leg 2*b*, 2*c*, and
   the wires 1*b*1-1*bn* each wound around the first leg 2*b* in a given layer (level) in the order from the tip 2*s* to the base 2*k* of the first leg 2*b* are respectively connected, in an order from the base 2*l* to the tip 2*t* of the second leg 2*c*, to the wires 1*c*1-1*cn* each wound around the second leg 2*c* in a layer (level) corresponding to the given layer.

6. Another Embodiment Relates to the Conductors 1*b*', 1*c*' of the Magnetic Stimulation Device a (Straight Connection Structure of a Second Embodiment: FIG. 13).
   In the magnetic stimulation device A according to any one of items 1 to 3,
   each of the conductors 1*b*', 1*c*' is composed a plurality of layers, each of which is formed of a wire, and the wires 161'-1*bn*'/1*c*l'-1*cn*' of the layers are wound around the leg 2*b*, 2*c* in a nested manner in an order from an inner layer to an outer layer, and
   the wires 1*b*1'-1*bn*' each wound around the first leg 2*b* in a given layer in the nest in the order from the inner layer to the outer layer are respectively connected to the wires 1*c*l'-1*cn*' each wound around the second leg 2*c* in a layer at a same position as the given layer in the nest.

7. Another Embodiment Relates to the Conductors 1*b*', 1*c*' of the Magnetic Stimulation Device a (Cross Connection Structure of the Second Embodiment: FIG. 14).
   In the magnetic stimulation device A according to any one of items 1 to 3,
   each of the conductors 1*b*', 1*c*' is composed of a plurality of layers, each of which is formed of a wire, and the wires 1*b*1'-1*bn*'/1*c*l'-1*cn*' of the layers are wound around the leg 2*b*, 2*c* in a nested manner in an order from an inner layer to an outer layer, and
   the wires 1*b*1'-1*bn*' each wound around the first leg 2*b* in a given layer in the nest in the order from the inner layer to the outer layer are respectively connected, in an order from the outer layer to the inner layer, to the wires 1*c*l'-1*cn*' each wound around the second leg 2*c* in a layer corresponding to the given layer in the nest.

8. Another Embodiment Relates to a General Configuration of the Magnetic Stimulation Device A.
   The magnetic stimulation device A includes: a magnetic core 2; conductors 1*b*, 1*c*; a fan 5 for delivering air; and a casing 4 that houses the magnetic core 2, the conductors 1*b*, 1*c*, and the fan 5.
   In the magnetic stimulation device A,
   the magnetic core 2 includes: a core body 2*a*; and first and second legs 2*b*, 2*c* extending in one direction from the core body 2*a* and each having such a shape that a distance L between opposite medial surfaces 2*m*, 2*n* of the legs 2*b*, 2*c* gradually increases from a base 2*k*, 2*l* to a tip 2*s*, 2*t* of the leg 2*b*, 2*c*, the magnetic core 2 being a stack of thin sheets 3 in which the sheets 3 are stacked one on top of another,
   the conductors 1*b*, 1*c* includes: a conductor 1*b* that is wound around the first leg 2*b* in a coil shape; and a conductor 1*c* that is wound around the second leg 2*c* in a coil shape, and
   the fan 5 is placed to face a space between the opposite medial surfaces 2*m*, 2*n* of the legs 2*b*, 2*c*.

Advantageous Effects of the Invention

In the magnetic core 2 of the present invention, the first and second legs 2*b*, 2*c* each have such a shape that a cross-sectional area Sb, Sc of the leg 2*b*, 2*c* gradually decreases from a base 2*k*, 2*l* of the leg 2*b*, 2*c* near the core body 2*a* to a tip 2*s*, 2*t* of the leg 2*b*, 2*c*. Therefore, the leakage of a magnetic flux G between the magnetic poles from the tip regions can be reduced, so that the density of the magnetic flux generated from the tips $2s$, $2t$ of the legs and effective for the treatment can be maintained constant. In addition, the shape of the legs also contributes to suppression of a temperature rise in the conductors $1b$, $1c$ ($1b'$, $1c'$) (FIG. 6). It should be noted that to avoid complexity, the conductor(s) $1b$, $1c$ ($1b'$, $1c'$) are sometimes referred to simply as "conductor(s) 1".

Furthermore, spaces are formed between the sloping medial surfaces of the legs $2b$, $2c$ and the conductors 1. Therefore, when a cooling gas 6 is introduced, the gas comes into these spaces and cool the legs $2b$, $2c$ effectively.

In the above-described device A, the first and second legs $2b$, $2c$ each have such a shape that a distance L between the opposite medial surfaces $2m$, $2n$ of the legs $2b$, $2c$ gradually increases from the base $2k$, $2l$ to the tip $2s$, $2t$. In this case, the density of a magnetic flux G1 generated from the tips $2s$, $2t$ on the inner edges near the medial surfaces $2m$, $2n$ is lower than that generated when the distance L is not increased, while a magnetic flux G3 generated from the tips $2s$ and $2t$ on the opposite outer edges far from the medial surfaces reaches deeper inside than that generated when the distance L is not increased. As a result, stimulation to the shallow part of the affected region like the skin is reduced while stronger stimulation is applied deep inside the affected region (the motor points P in the muscle to be treated), and thereby discomfort of the patient can be reduced (FIG. 3).

In the magnetic core 2, the thin sheets 3 are stacked so that the surface of each of the stacked sheets 3 is parallel to a plane M passing through both of the core body $2a$ and the legs $2b$, $2c$. In this case, eddy current U to be generated in the legs $2b$, $2c$ is suppressed by the interlayer insulation of the legs $2b$, $2c$, and thereby a temperature rise in the legs $2b$, $2c$ is suppressed (FIG. 9).

In the casing 4, cooling spaces 81 are provided between the medial surfaces $2m$, $2n$ of the legs $2b$, $2c$ and the conductors 1 wound around the legs $2b$, $2c$. In this case, the cooling gas 6 from the fan 5 can be used to cool the legs $2b$, $2c$ more effectively (FIG. 8).

As one example of the structure of the conductors 1, the conductors 1 are each divided into a plurality of layers (levels) in the longitudinal direction of the legs $2b$, $2c$, or the conductors 1 are each composed of a plurality of layers arranged in a radially nested manner. In this case, the current densities in the respective layers are levelled and thus a local temperature rise is suppressed.

Unlike the "straight connection", in the case of "cross connection (in the case where the respective layers are "cross-connected"), the electromotive force generated in the coil located closer to the tip (or on the inner side) and that generated in the reverse direction in the coil located closer to the base (or on the outer side) cancel each other out. Thus, the temperature rise in the conductors 1 is suppressed more effectively.

Due to a combination of these improvements (in the shape and stacking direction of the magnetic core 2, the cooling method, and the structure of the conductors 1), even if the size of the device is reduced, a temperature rise in the conductors 1 and the magnetic core 2 can be reduced to a value lower than the legal limit, and in addition, the level of the magnetic flux density and the number of pulses of the stimulation required for the treatment can be achieved.

BRIEF DESCRIPTION OF DRAWINGS

FIG. 1 is a perspective view of a magnetic stimulation device of the present invention, taken from a lid side.

FIG. 2 is a horizontal cross sectional view of an internal structure of FIG. 1, taken from the lid side.

FIG. 3 is a cross sectional view taken along line XX of FIG. 2.

FIG. 4 is a central longitudinal cross sectional view of the magnetic stimulation device of the present invention.

FIG. 5 is a perspective view of one of the thin sheets of the magnetic core of the present invention.

FIG. 6 is a perspective view showing a horizontal cross section of the legs of the magnetic core of the present invention.

FIG. 7 is a perspective view showing the stacking direction of the thin sheets of the magnetic core of the present invention.

FIG. 8(a) is a diagram showing the relative positions of the magnetic core and the conductors of the present invention, and FIG. 8(b) is a diagram showing the relative positions of the magnetic core and the other conductors of the present invention.

FIG. 9 is a diagram showing the relationship between an eddy current and a magnetic flux generated between the magnetic poles in FIG. 8.

FIG. 10 is a schematic view of a connection structure of conductors (single coil) of the present invention.

FIG. 11(a) is a schematic view of a connection structure of conductors (straight connection structure of a first embodiment), and FIG. 11(b) is a schematic front view of the structure.

FIG. 12(a) is a schematic view of a connection structure of conductors (cross connection structure of the first embodiment), and FIG. 12(b) is a schematic front view of the structure.

FIG. 13(a) is a schematic view of a connection structure of conductors (straight connection structure of a second embodiment), and FIG. 13(b) is a schematic front view of the structure.

FIG. 14(a) is a schematic view of a connection structure of conductors (cross connection structure of the second embodiment), and FIG. 14(b) is a schematic front view of the structure.

FIG. 15 is a diagram showing the relationship between an opening angle between the opposite medial surfaces of the magnetic core of the present invention and results of magnetic stimulation at two different points of an affected region.

DESCRIPTION OF EMBODIMENTS

Next, the present invention will be described in detail by way of embodiments. These embodiments are given for easy understanding by those skilled in the art. That is, it is to be understood that the present invention should not be limited only by these embodiments but should be limited only by the technical idea described in the entire specification of the present invention.

A continuous magnetic stimulation device A of the present invention includes conductors 1, a magnetic core 2, a casing 4, and a cooling mechanism 7. The conductors 1 are respectively wound around left and right legs $2b$, $2c$ of the magnetic core 2 in a coil shape.

The magnetic core 2 is a U-shaped member and includes a cubic or cuboidal core body $2a$ and legs $2b$, $2c$ extending axially symmetrically in the same direction from opposite ends of a surface of the core body $2a$. The magnetic core 2 is a stack of thin sheets 3 to be described later.

The legs $2b$, $2c$ each have such a shape that a cross-sectional area Sb, Sc of the leg $2b$, $2c$ cut by a plane K (for example, a horizontal plane) that is parallel to the core body 2a and passes through both of the legs 2b, 2c gradually decreases toward a tip 2s, 2t of the leg 2b, 2c.

An embodiment shown in FIG. 6 is an example of the leg shape. The opposite medial surfaces 2m, 2n of the legs 2b, 2c are both flat surfaces, and the distance L between the surfaces 2m, 2n gradually increases from the bases 2k, 2l to the tips 2s, 2t. The angle indicating the distance between the opposite medial surfaces 2m, 2n is referred to as an "opening angle" and denoted by "e" (FIG. 5).

More specifically, the shape of each of the legs is a truncated pyramid or a solid having a trapezoidal shape in front view with a vertical lateral surface and a sloping medial surface so that the distance between the opposite medial surfaces (flat surfaces) increases towards the top of the leg.

The magnetic core 2 is a stack of many thin sheets 3 of rolled silicon steel, each coated with a thin insulating layer, as shown in FIG. 5. In this embodiment, 0.35 mm-thick rolled silicon steel sheets are used. The thin sheet 3 shown in FIG. 5 is one example.

As shown in FIG. 7, the thin sheets 3 are stacked in parallel to a plane M (for example, a vertical plane) passing through both of the core body 2a and the legs 2b, 2c of the magnetic core 2 (in other words, the thin sheets 3 are stacked one on top of another). Therefore, as shown in FIG. 5, the shape of each sheet 3 is an approximate U shape including a sheet body 3a and two leg-forming protruding pieces 3b, 3c extending in the same direction from one side of the sheet body 3a, and the distance between the opposite medial sides of the leg-forming protruding pieces 3b, 3c gradually increases from the bases to the tips. The "opening angle" indicating the distance between them is denoted by θ.

The distribution of magnetic fluxes G generated from the tips 2s, 2t of the legs 2b, 2c varies depending on the above-mentioned opening angle θ of the magnetic core 2. More specifically, as shown in FIG. 3, when the distance between the opposite medial surfaces 2m, 2n of the legs 2b, 2c is large, a magnetic flux G1 generated from the tip regions near the medial surfaces 2m, 2n is lower than that generated when the opening angle θ is 0, while a magnetic flux G3 generated from the tips 2s, 2t on the opposite outer edges far from the medial surfaces reaches deeper inside than that generated when the opening angle θ is 0. As a result, as shown in FIG. 3, stimulation to the shallow part of the body is reduced while the motor points P deep inside the body are stimulated more strongly.

Now, when the motor points P deep inside the body are located at a depth of 20 mm from the skin surface and the external nociceptors found in the skin are located at a depth of 1 mm, FIG. 15 reveals that the opening angle θ should be in a range of 9.1° to 17.7°, and preferably in a range of 13.5°±2°. Here, the depth from the skin surface is denoted by Z.

At an angle of θ=9.1°, an increase in the intensity of the magnetic stimulation at a depth Z of 20 mm (the induced current density $A/m^2$ at a depth of 20 mm, i.e., the intensity of the eddy current at that location) turns to slow down, and at an angle of θ=17.7°, both the intensities of the magnetic stimulation at a depth Z of 20 mm and a depth Z of 1 mm turn sharply downward. At an angle of θ=13.5°, the intensity of the magnetic stimulation at a depth Z of 20 mm hits a peak. The values of the intensity of the magnetic stimulation at a depth Z of 20 mm reach a plateau in a range of 9.1° to 17.7°. When the angle exceeds 17.7°, the intensity of the magnetic stimulation decreases sharply.

Since the highest intensity ($A/m^2$) of magnetic stimulation at a depth Z of 20 mm is included in the range of 13.5°±2° and that intensity is maintained almost constant in this range, the most appropriate opening angle θ falls within this range.

The intensity of magnetic stimulation at a depth of 1 mm decreases gradually and constantly as the opening angle θ increases. In the above range, the intensity of stimulation to the skin is reduced slightly compared to that at an opening angle θ of 0.

In FIG. 15, the left vertical axis indicates the induced current density $A/m^2$ at a depth of 20 mm from the skin, the right vertical axis indicates the induced current density $A/m^2$ at a depth of 1 mm from the skin, and the horizontal axis indicates the opening angle θ (degrees) between the opposite medial surfaces 2m, 2n of the magnetic core 2.

A wire as a material of the conductors 1 is a long, flat rectangular copper plates (strip) with a rectangular or square cross-section. The conductors 1 are formed of the wires respectively wound in a coil shape around the legs 2b, 2c of the magnetic core 2. The conductor 1 is sometimes referred to as a coil. The surface of the conductor 1 is coated with an insulating layer.

The wires of the conductors 1 are each closely wound so that the inner and outer coils and the upper and lower coils are in contact with each other (of course, it is also possible to wind the coils such that a space for cooling the coils (not shown) is formed between the inner and outer coils to prevent the coils from coming in contact with each other).

The insulating coating is made of a urethane resin and its thickness is reduced to allow heat dissipation from the surface of the conductors 1. In this embodiment, the thickness of the insulating coating is 20 μm.

There are two types of wires used for the conductors 1. One is a single wide flat rectangular wire (strip) that covers almost the entire surface of the legs 2b, 2c, as shown in FIG. 8(a). The other is a narrower flat rectangular wire, as shown in FIG. 8(b). In the latter case, a plurality of flat rectangular wires are wound around the legs 2b, 2c in a multi-layer and/or multi-turn configuration. There are three patterns of winding the wires of the conductors 1 around the legs 2b, 2c. There are two methods of connecting the conductors 1b, 1c (1b', 1c') formed of flat rectangular wires wound around the legs 2b, 2c, respectively, to be described later. (It should be noted that wires having a circular cross section can be used instead of narrower rectangular wires.)

(Patterns of Winding Wires of Conductors 1 Around Legs 2b, 2c)

In the first winding pattern, as shown in FIG. 8(a) and FIG. 10, a single wide wire is wound around each of the legs 2b, 2c with multiple turns from inside to outside. The outermost coils are connected together and the innermost coils are respectively connected to the excitation current supply lines 10b, 10c. This is referred to as a "single coil".

In the second and third winding patterns, as shown in FIG. 8(b), a plurality of narrower flat rectangular wires are wound around each of the legs 2b, 2c in a vertical multi-layer (multi-level) configuration and/or in a multi-turn nested configuration. The former is referred to as a "parallel coil" and the latter is referred to as a "nested coil".

Thus, there are three patterns of winding the wires of the conductors 1 around the legs 2b, 2c: a "single coil", a "parallel coil", and a "nested coil".

The above second "parallel coil" includes a coil having upper and lower two layers as shown in FIG. 3 and FIG. 4 and a coil having multiple layers (levels) as shown in FIG. 11 and FIG. 12.

The above third "nested coil" is a coil in which a plurality of narrower flat rectangular wires are respectively wound around the legs $2b$, $2c$ in a radial multi-layer (multi-turn) configuration, as shown in FIG. 13 and FIG. 14. In other words, the coils from the inner layer to the outer layer are wound in a nested manner around the legs $2b$, $2c$, respectively.

In any of the "single coil", the "parallel coil", and the "nested coil", the wire is wound in such a manner that the direction N (S) of the magnetic field in the first leg $2b$ is opposite to the direction S (N) of the magnetic field in the second leg $2c$. More specifically, when the conductor $1b$ is wound clockwise around the first leg $2b$, the conductor $1c$ is wound counterclockwise (FIG. 10 to FIG. 14).

Next, the connection structures of the wires arranged in multiple levels or layers in the "parallel coil" and the "nested coil" will be described. FIG. 11 and FIG. 13 show a wire connection structure in the "parallel coil and the "nested coil". This is referred to as a "straight connection structure". On the other hand, FIG. 12 and FIG. 14 show another wire connection structure in the "parallel coil" and the "nested coil". This is referred to as a "cross connection structure". These connection structures will be described respectively.

In the "straight connection structure (FIG. 11)" of the "parallel coil", the outermost coils in the layers at the same vertical position (i.e., the layers adjacent to each other) $1b1/1c1$ to $1bn/1cn$ are connected together to form a single wire, and the ends of the innermost coils in the same layers are respectively bundled and connected to the excitation current supply lines $10b$, $10c$.

In the "cross connection structure (FIG. 12)" of the "parallel coil", the outermost coils $1b1/1c1$ in the first layers (or at the first level) near the tips $2s$, $2t$ are respectively cross-connected to the coils $1bn/1cn$ in the nth layers near the bases $2k$, $2l$ to form a single wire, and the outermost coils $1b2/1c2$ in the second layers are respectively connected to the coils $1b(n-1)/1c(n-1)$ in the n-lth layers to form a single wire. The following coils are connected in the same manner. In this case, the coils in different layers are connected. Then, the ends of the innermost coils are respectively bundled and connected to the excitation current supply lines $10b$, $10c$.

In the "straight connection structure (FIG. 13)" of the "nested coil, the first wire is wound several times around and along the outer periphery of the first leg $2b$ from the tip $2s$ toward the base $2k$ of the first leg $2b$. This coil in the innermost layer is denoted by $1b1'$.

Next, the second wire is wound on the innermost first coil $1b1'$ as the innermost layer. The "n" wires are wound one after another in a nested manner to form "n" layers. The coil in the outermost layer is denoted by $1bn'$.

Likewise, the rest of the first wire to the rest of the nth wire are wound around and along the outer periphery of the second leg $2c$ one after another in a nested manner. The coils around the second leg $2c$ are denoted by $1c1'$ to $1cn'$.

The innermost coils $1b1'$ and $1c1'$ in the innermost layers are connected together, the coils in the layers at the same position in the nests are connected one after another, and the outermost coils $1bn'$ and $1cn'$ in the outermost layers are connected together. Then, the ends of the coils on the first leg $2b$ and the ends of the coils on the second leg $2c$ are respectively bundled and connected to the excitation current supply lines $10b$, $10c$.

In the "cross connection structure (FIG. 14)" of the "nested coil", the wires are wound in the same nested manner, but the connection structure is different from the above structure.

The coil $1b1'$ in the innermost layer near the base $2k$ of the first leg $2b$ is connected to the coil $1cn'$ in the outermost layer near the tip $2t$ of the second leg $2c$ to form a single wire. Likewise, the coil $1b2'$ in the second layer from the innermost layer near the base $2k$ of the first leg $2b$ is connected to the coil $1c$ $(n-1)'$ in the second layer from the outermost layer near the tip $2t$ of the second leg $2c$. The coil $1bn'$ in the outermost nth layer near the base $2k$ of the first leg $2b$ is connected to the coil $1c1'$ in the innermost layer near the tip $2t$ of the second leg $2c$. Then, the ends of the coils wound around the first leg $2b$ and the ends of the coils wound around the second leg $2c$ are respectively bundled and connected to the excitation current supply lines $10b$, $10c$.

The relationship between the legs $2c$ and the conductors $1b$, $1c$ will be described. In the embodiment of FIG. 8, spaces having a right triangular cross section and gradually increasing toward the tips $2s$, $2t$ are formed between the opposite outward-sloping medial surfaces $2m$, $2n$ and the inner peripheries of the conductors $1b$, $1c$. These spaces are referred to as cooling spaces 81.

Since the surface of the conductor 1 is covered with an insulating coating, as described above, and the conductor 1 itself generates less heat as a whole, as described later, there is no particular need to provide cooling gaps, which are conventionally required, between the layers of the conductor 1, and thus they can be wound in close contact with each other. The cooling gaps are provided between the layers of the conductor 1 only when there is a particular need. In FIG. 4, the gaps between the coils in the upper and lower layers and between the coils in the inner and outer layers are exaggeratedly illustrated, but in fact, there is little gap between them.

The casing 4 for housing the magnetic core 2, coil-shaped conductors 1, a cooling fan 5 serving as a part of the cooling mechanism 7, etc. is made of a resin (ABS here). This casing 4 includes a casing body 46 with a top opening, a lid 41 that covers the opening, and a handle 49. The lid 41 is fastened with bolts (not shown) to close the top opening.

The handle 49 is provided on the bottom 48 of the casing body 46 and extends backward from the casing 4. An air intake port 47 communicating with the interior space is provided on the front surface of the casing body 46.

The magnetic flux generation surface 42 of the lid 41, which is to be brought into contact with the affected region of the patient's body, has two parallel rectangular raised portions 43 bulging outward and extending in the longitudinal direction of the casing 4. The undersides of the raised portions 43 are shallow recesses corresponding to the raised portions 43. The tips $2s$, $2t$ of the legs $2b$, $2c$ of the magnetic core 2 are fitted into the recesses on the undersides of the rectangular raised portions 43 (FIG. 3).

Rows of horizontal slits serving as an air outlet port 44 are formed on the front surface of the lid 41. The position of this air outlet port 44 corresponds to the position of the space between the legs $2b$, $2c$ of the magnetic core 2. A cord attachment 45 extending backward is provided on the rear surface of the lid 41. A power cord 50 is connected to this cord attachment 45.

The magnetic core 2 enclosed in the casing 4 is pressed against the lid 41 by a support 51 on a columnar member standing on the bottom 48 of the casing body 46. An air intake space 83 communicating with the air intake port 47 is provided between the support 51 and the bottom 48.

In a fan storage space 84 formed behind the magnetic core 2, this air intake space 83 communicates with the above-mentioned cooling spaces 81 formed on the outlet side.

The fan 5 is mounted in the fan storage space 84 behind the magnetic core 2. The cooling mechanism 7 is composed of these air intake port 47, cooling spaces 81, fan storage space 84, air intake space 83, air outlet port 44, and fan 5. (Instead of the fan 5, an air supply hose (not shown) may be connected to the air intake port 47).

Next, the operation of the device A will be described. The type of the coil in the device A is a "single coil", as shown in FIG. 8(*a*) and FIG. 10. Other types of coils will be described, focusing on the differences from the "single coil".

In FIG. 10, when an excitation current (a pulse current or an alternating current) is supplied from one excitation current supply line 10*b*, the excitation current flows counterclockwise through the conductor 1*b* wound around the first leg 2*b*, subsequently flows clockwise through the conductor 1*c* wound around the second leg 2*c*, and then flows to the other excitation current supply line 10*c*.

As a result, the tip 2*s* of the first leg 2*b* has a south(S) magnetic pole, while the tip 2*t* of the second leg 2*c* has a north (N) magnetic pole. When the flow of the excitation current in one direction ends, the flow is reversed. When the excitation current flows in the opposite direction from the other excitation current supply line 10*c*, flows clockwise through the conductor 1*c* wound around the second leg 2*c*, subsequently flows counterclockwise through the conductor 1*b* wound around the first leg 2*b*, and then flows to the one excitation current supply line 10*b*. As a result, the tip 2*t* of the second leg 2*c* has a south(S) magnetic pole, while the tip 2*s* of the first leg 2*b* has a north (N) magnetic pole, which means that the magnetic polarity is reversed. This is repeated at regular intervals. Magnetic fluxes G are generated between the tip 2*s* and the tip 2*t* of the magnetic core 2.

The magnetic fluxes G thus generated include a magnetic flux G3 that reaches deeper inside the affected region (lower jaw region in the figure) than that generated at an opening angle $\theta=0$ and works in that deep region and a magnetic flux G1 that is weaker than that generated at an opening angle $\theta=0$ and works on the skin. Thus, stronger eddy current U3 is generated deep inside the affected region and gives magnetic stimulation to that region, while weaker eddy current U1 is generated on the skin and gives magnetic stimulation to that region.

A comparison with a conventional magnetic core is as follows. In the conventional magnetic core, since the legs have a prismatic shape with a constant cross sectional area, leakage of magnetic flux between the magnetic poles of the legs increases toward the tips. Therefore, due to this leakage magnetic flux, local eddy currents are generated in the regions of the conductors 1 near the tips 2*s*, 2*t*. As a result, the temperature of these regions is higher than the legal limit.

The legs 2*b*, 2*c* of the magnetic core 2 of the present device A each have such a shape that the cross-sectional area Sb, Sc of the leg gradually decreases from the base 2*k*, 2*l* near the core body 2*a* to the tip. Therefore, leakage of magnetic flux between the magnetic poles from the tip regions of the medial surfaces is reduced. As a result, eddy current U does not occur in the conductors 1, and a temperature rise in the tip regions of the conductors 1 is suppressed. At the same time, since the leakage of magnetic flux as described above is also reduced, the density of the magnetic flux generated from the tips 2*s*, 2*t* can be maintained constant. As a result, energy loss can be reduced, which contributes to reduction in device size.

In particular, when the distance between the opposite medial surfaces 2*m*, 2*n* of the legs 2*b*, 2*c* is large, as shown in FIG. 3, the density of the magnetic flux G1 generated from the tip regions near the opposite medial surfaces 2*m*, 2*n* is lower and the magnetic flux G3 generated on the tip regions near the lateral surfaces reaches deeper than that generated at an opening angle $\theta=0$. Therefore, stronger magnetic stimulation can be given to the deep part of the affected region (i.e., the motor points P of the muscles to be treated), while mild stimulation can be given to the shallower part of the affected region like the skin, and discomfort of the patient can be reduced.

As a result, the large contraction of the jaw muscles (or arm muscles) can be induced without pain, and the jaw or arm muscles can be effectively trained for normal swallowing.

When the magnetic core 2 is a stack of thin sheets 3 in which the sheets 3 are placed one on top of another, i.e., when the thin sheets 3 are stacked such that the surface of the stacked sheets are parallel to a plane (vertical plane) M passing through both of the core body 2*a* and the legs 2*b*, 2*c* of the magnetic core 2, the direction of the magnetic flux generated between the magnetic poles of the first leg 2*b* and the second leg 2*c* (or the second leg 2*c* and the first leg 2*b*) during current supply is perpendicular to the stacking direction of the thin sheets 3, and thus the eddy current path is interrupted by the interlayer insulation of the legs 2*b*, 2*c* (insulating films on the sheets 3), and generation of eddy current U is suppressed (FIG. 9). As a result, a temperature rise in the legs 2*b*, 2*c* is suppressed.

During current supply, the cooling mechanism 7 continues to work (i.e., the fan 5 and the air supply hose work to introduce and remove air). The cooling gas (air) 6 flows into the air intake space 83 through the air intake port 47 and is then delivered to the cooling spaces 81 by the fan 5. The cooling air 6 flowing in the cooling spaces 81 comes into direct contact with the conductors 1 and the legs 2*b*, 2*c* of the magnetic core 2, draws the heat from the conductors 1 and the legs 2*b*, 2*c* of the magnetic core 2, and then is forced out through the air outlet port 44.

Since the front and rear sides of the cooling space 81 are blocked by the conductor 1, the cooling air 6 hits the conductor 1, creates sufficient turbulence within the cooling space 81, and as a result, produces high cooling effect.

As described above, as a result of improvements in the stacking direction and shape of the magnetic core 2 as well as improvements in the cooling mechanism, the temperature of the device is reduced below 43° C. as the safety limit, even if successive magnetic pulses (6,000 pulses in total) are generated in 15 minutes at room temperature of 25° C. Thus, thermal risk to the patient can be prevented.

Next, the relationship between the suppression of temperature rise and improvements in the connection structure in addition to the above-described improvements will be described.

In a "single coil" as shown in FIG. 8(*a*), when an excitation current is supplied, the inductance of the tip regions of the legs 2*b*, 2*c* of the magnetic core 2 are locally lower than that of the base regions thereof, as described above. Therefore, the flow of the excitation current concentrates on the upper edge regions of the wide conductors 1*b*, 1*c* located in front of the tip regions of the legs 2*b*, 2*c*. As a result, in the case of a "single coil", the temperature rise of the device is suppressed by improvements in the stacking direction and shape of the magnetic core 2 in addition to the above-described air cooling as a main cooling means.

Then, improvements in the conductors 1*b*, 1*c* designed to suppress a temperature rise will be described. In this case, the conductors 1*b*, 1*c* are each divided into a plurality of layers (levels) in the longitudinal direction of the legs 2*b*, 2*c*, or the conductors 1$b$, 1$c$ are each composed of a plurality of layers in the radial direction. Then, unlike a "single coil", the concentration of the current density to the regions near the tips 2$s$, 2$t$ can be reduced, and as a result, the current densities in the respective layers are levelled and thus a temperature rise in each layer is further suppressed. A brief description of this mechanism is given below.

When an excitation current is supplied to the conductors 1$b$, 1$c$, the tip 2$s$ of the first leg 2$b$ has a north (N) (or south (S)) magnetic pole, while the tip 2$t$ of the second leg 2$c$ has a south (S) (or north (N)) magnetic pole, which is opposite to that of the tip 2$s$. Thus, the magnetic polarity is reversed, and a magnetic flux G is generated between the two poles. This is true throughout the present invention.

(Straight Connection of Parallel Coil: FIG. 11)

In the first connection structure (straight structure of a parallel coil), when a current is supplied, the inductance of the tip regions of the legs 2$b$, 2$c$ is lower than that of the regions near the bases 2$k$, 2$l$ thereof. Therefore, the amount of excitation current flowing in the coils 1$b$1/1$c$1 to 1$bn$/1$cn$ wound around the legs 2$b$, 2$c$ decreases from the tips 2$s$, 2$t$ toward the bases 2$k$, 2$l$. This means that the amount of excitation current flowing in the first layers 1$b$1/1$c$1 wound around the tip regions of the legs 2$b$, 2$c$ is greater than that flowing in the second and the following layers 1$b$2-1$bn$/1$c$2-1$cn$ closer to the bases 2$k$, 2$l$. However, unlike a "single coil" formed of a single wide flat rectangular wire, the conductors 1$b$, 1$c$ are each divided into a plurality of wires and therefore the bias in the current density is reduced.

In the magnetic core 2 of the present invention, the inter-pole leakage magnetic flux between the legs 2$b$, 2$c$ is significantly reduced, as described above. Therefore, generation of eddy currents is also reduced in each of the conductive layers 1$b$1-1$bn$/1$c$1-1$cn$.

As a result, in the "straight structure of a parallel coil", the bias of the current density is reduced compared with that of a "single coil", and therefore, heat generation in the conductors 1$b$, 1$c$ is also significantly reduced compared with that in a "single coil".

(Cross Connection of Parallel Coil: FIG. 12)

Next, the second connection structure of the first embodiment (cross structure of a parallel coil) will be described (FIG. 12). When an excitation current is supplied to the conductors 1$b$, 1$c$, its flow tends to be slightly biased toward the first layers 1$b$1/1$c$1 due to the difference in the inductance, as described above. However, in the nth layers 1$bn$/1$cn$ located near the bases 2$k$, 2$l$ and connected to the first layers 1$b$1/1$c$1, the excitation current is harder to flow than in the first layers 1$b$1/1$c$1, and therefore the amount of excitation current flowing in the first layers 1$b$1/1$c$1 is reduced as the nth layers 1$bn$/1$cn$ serve as limiting factors. In other words, the amount of the excitation current flowing in the first layers 1$b$1/1$c$1 is equal to that flowing in the nth layers 1$bn$/1$cn$. Thereby, an almost constant and suppressed excitation current flows throughout the respective layers of the conductors 1. As a result, heat generation can be suppressed more than in the above-described first connection structure.

It should be noted that the "parallel coil" includes a vertical two-layer structure of FIG. 3 and FIG. 4, and the "straight connection" and "cross connection" structures are applied to the parallel coil.

(Straight Connection of Nested Coil: FIG. 13)

Next, the first connection structure of the second embodiment (straight structure of a nested coil) will be described. The conductors 1$b'$, 1$c'$ are each composed of a plurality of wires that are closely wound around the legs 2$b$, 2$c$ in the form of concentric coil springs of different diameters from small to large, i.e., in a multi-turn configuration, as described above. More specifically, the layers of the conductors 1$b'$, 1$c'$ are arranged in a nested manner, with layers of smaller diameters being nested within layers of larger diameters. Like the "straight structure" of the first embodiment, the wires of the conductive layers 1$b$1'-1$bn'$ wound around the first leg 2$b'$ are respectively connected in parallel to the wires of the conductive layers 1$c$1'-1$cn'$ wound around the second leg 2$c'$.

When an excitation current is supplied to the conductors 1$b'$, 1$c'$, the excitation current flows downwardly (or upwardly) through the nested conductive layers 1$b$1'-1$bn'$/1$c$1'-1$cn'$ around the legs 2$b$, 2$c$. In this case, due to a difference in inductance as described above, the base regions of the legs 2$b$, 2$c$ serve as limiting factors, the bias of the current density in the conductive layers 1$b$1'-1$bn'$/1$c$1'-1$cn'$ is significantly reduced.

(Cross Connection of Nested Coil: FIG. 14)

The second connection structure of the second embodiment (cross structure of a nested coil) is as follows. The innermost first layer 1$b$1' of the layers wound around the first leg 2$b$ with multiple turns is connected to the outermost nth layer 1$cn'$ of the layers wound around the second leg 2$c$, and the outermost nth layer 1$bn'$ of the layers wound around the first leg 2$b$ is connected to the innermost first layer 1$c$1' of the layers wound around the second leg 2$c$. In such a manner, the layers wound around the first leg 2$b$ are respectively connected to the layers wound around the second leg 2$c$ in reverse order.

When a current is supplied, the inductance of the tip regions of the legs 2$b$, 2$c$ is lower than that of the base regions, as described above. The effect of this phenomenon also becomes more pronounced in the inner layers located near the tips in the radial direction.

In other words, when the tip regions of the first layers 1$b$1'/1$c$1' are compared with the tip regions of the outermost layers 1$bn'$/1$cn'$, the first layers 1$b$1'/1$c$1' are more affected by this phenomenon. As a result, the intensity of the excitation current flowing in the first layers 1$b$1'/1$c$1' is slightly higher than that flowing in the outermost layers 1$bn'$/1$cn'$. Therefore, in the case of this reverse connection, the base regions of the nth layers 1$bn'$, 1$cn'$, which are least affected by the inductance, serve as limiting factors, and the bias of the current density is reduced further and the temperature rise can be suppressed more effectively.

As described above, in the case of "cross connection" of the layers, the electromotive force generated in the wire located closer to the tip (or on the inner side) and that generated in the reverse direction in the wire located closer to the base (or on the outer side) cancel each other out. Thus, the temperature rise in the conductors 1$b$, 1$c$ is further suppressed than in the case of "straight connection" of the layers.

As described above, as a result of improvements in the connection structure in addition to improvements in the stacking direction and shape of the magnetic core 2 and the cooling mechanism, a small magnetic stimulation device A can be used to apply magnetic stimulation of 100 sessions (6,000 pulses) to a patient with a small jaw within 6 minutes and 40 seconds, which is significantly shorter than 15 minutes required by the specification. As a result, the burden on the patients and therapists can be reduced significantly.

LIST OF REFERENCE SIGNS

A: Continuous magnetic stimulation device
G, G1, G3: Magnetic fluxes

L: Distance between medial surfaces
K, M: planes
P: Motor point
θ: Opening angle
1, 1b, 1c (1b', 1c'): Conductors
1b1-1bn/1c1-1cn (1b1'-1bn'/1c1'-1cn'): Coils (layers, levels)
2: Magnetic core
2a: Core body
2b, 2c: Legs
2k, 2l: Bases
2m, 2n: (Opposite) medial surfaces
2s, 2t: Tips
3: Thin sheet
3a: Sheet body
3b, 3c: Leg-forming protruding pieces
4: Casing
5: Fan
6: Cooling gas (air)
7: Cooling mechanism
10b, 10c: Excitation current supply lines
41: Lid
42: Magnetic flux generation surface
43: Raised portion
44: Air outlet port
45: Cord attachment
46: Casing body
47: Air intake port
48: Bottom
49: Handle
50: Power cord
51: Support
81: Cooling space
83: Air intake space
84: Fan storage space

The invention claimed is:

1. A magnetic stimulation device comprising:
a magnetic core including: a core body; and first and second legs extending in one direction from the core body;
conductors including:
a conductor that is wound around the first leg in a coil shape; and
a conductor that is wound around the second leg in a coil shape; and
a casing that houses the magnetic core and the conductors, wherein
the first and second legs each are configured to have such a shape that a distance between opposite medial surfaces of the legs gradually increases from bases of the legs near the core body to tips of the legs, and thereby the first and second legs each have such a shape that each cross-sectional area of the legs parallel to a plane passing horizontally through both of the legs gradually decreases from the bases to the tips so that a leakage of magnetic flux between magnetic poles from the medial surfaces of the tips is reduced, and
each of the conductors is wound around each area of the legs, and each area is configured to have the shape that the distance between the opposite medial surfaces of the legs gradually increases.

2. The magnetic stimulation device according to claim 1, wherein the magnetic core is a stack of thin sheets, and a surface of each of the stacked sheets is parallel to a plane passing vertically through both of the core body and the legs of the magnetic core.

3. The magnetic stimulation device according to claim 1, further comprising a cooling space designed to allow a cooling gas taken into the casing to flow through, between the medial surface of each of the legs and a surface of each of the conductors wound around the legs to face the medial surface.

4. The magnetic stimulation device according to claim 1, wherein
each of the conductors is divided into a plurality of layers, each of which is formed of a wire, and the wires of the layers are wound around each of the legs in an order from the tip to the base of the each of the legs,
an ordinate number of the conductive layers is counted in such a manner that a layer located closest to the tip of the first or second leg is referred to as a first layer, a layer adjacent to the first layer toward the core body is referred to as a second layer, and a layer closest to the core body is referred to as an nth layer, and
the wires each wound around the first leg in a given layer are respectively connected to the wires each wound around the second leg in a layer adjacent to the given layer such that:
the first layer wound around the first leg is connected to the first layer wound around the second leg,
the nth layer wound around the first leg is connected to the nth layer wound around the second leg, and
remaining ends of the wires of the conductive layers wound around each of the first and second legs are connected in parallel for the individual first and second legs, respectively.

5. The magnetic stimulation device according to claim 1, wherein
each of the conductors is divided into a plurality of layers, each of which is formed of a wire, and the wires of the layers are wound around each of the legs in an order from the tip to the base of the each of the legs,
an ordinate number of the conductive layers is counted in such a manner that a layer located closest to the tip of the first or second leg is referred to as a first layer, a layer adjacent to the first layer toward the core body is referred to as a second layer, and a layer closest to the core body is referred to as an nth layer, and
the wires each wound around the first leg in a given layer in the order from the tip to the base of the first leg are respectively connected, in an order from the base to the tip of the second leg, to the wires each wound around the second leg in a layer corresponding to the given layer such that:
the first layer wound around the first leg is connected to the nth layer wound around the second leg,
the nth layer wound around the first leg is connected to the first layer wound around the second leg,
the second to (n−1)th layers wound around the first leg are respectively connected in reverse order to the (n−1)th to second layers around the second leg, and
remaining ends of the wires of the conductive layers wound around each of the first and second legs are connected in parallel for the individual first and second legs, respectively.

6. A magnetic stimulation device comprising:
a magnetic core;
conductors;
a fan for delivering air; and
a casing that houses the magnetic core, the conductors, and the fan, wherein
the magnetic core includes:
a core body; and first and second legs extending in one direction from the core body and each having such a shape that a distance between opposite medial surfaces of the legs gradually increases from bases to tips of the legs, the magnetic core being a stack of thin sheets in which the sheets are stacked one on top of another, the conductors include:
- a conductor that is wound around the first leg in a coil shape; and
- a conductor that is wound around the second leg in a coil shape, each of the conductors is wound around each area of the legs, and each area is configured to have the shape that the distance between the opposite medial surfaces of the legs gradually increases, and the fan is placed to face a space between the opposite medial surfaces of the legs.

\* \* \* \* \*